United States Patent [19]
Vince et al.

[11] Patent Number: 5,241,069
[45] Date of Patent: Aug. 31, 1993

[54] CARBONATE INTERMEDIATES FOR THE SYNTHESIS OF PURINE SUBSTITUTED CYCLOPENTENE DERIVATIVES

[75] Inventors: Robert Vince, Mendota Heights, Minn.; Mark L. Peterson, Maryland Heights, Mo.; John W. Lackey, Durham; Robert A. Mook, Jr.; John J. Partridge, both of Chapel Hill, all of N.C.

[73] Assignees: Glaxo Inc., Research Triangle Park, N.C.; Univeristy of Minnesoota, St. Paul, Minn.

[21] Appl. No.: 788,667

[22] Filed: Nov. 6, 1991

Related U.S. Application Data

[62] Division of Ser. No. 505,809, Apr. 6, 1990, Pat. No. 5,126,452.

[51] Int. Cl.$^5$ .................. C07D 473/18; C07D 473/40
[52] U.S. Cl. .................................................... 544/277
[58] Field of Search ............................... 544/277, 276

[56] References Cited

U.S. PATENT DOCUMENTS

| | | | |
|---|---|---|---|
| 4,916,224 | 4/1990 | Vince et al. | 544/254 |
| 5,057,630 | 10/1991 | Lackey | 544/276 |
| 5,126,452 | 6/1992 | Vince | 544/276 |

FOREIGN PATENT DOCUMENTS 2217320 10/1989 United Kingdom .

OTHER PUBLICATIONS

March, J., *Advanced Organic Chemistry*, 3rd Ed., Chap. 4 John Wiley & Sons, New York, N.Y.(1985).
Vince, R., et al., *Biochem. Biophys. Res. Commun.* 156 (2) 1045 (1988).
*J. Am. Chem. Soc.*, 110, 621 (1988).
*Synthesis*, Sugai, T., et al., 19–22 (1988).
J.C.S. Perkin I, Bajorek, R., 1, 1243 (1974).

*Primary Examiner*—Mark L. Berch
*Attorney, Agent, or Firm*—Charles T. Joyner

[57] ABSTRACT

This invention relates to the new process for preparing the 1R-cis isomer of carbovir, (1R-cis)-amino-1,9-dihydro-9-[4-(hydroxymethyl)-2-cyclopenten-1-yl]-6H-purin-6-one, an antiviral agent and intermediates of the formula (VIb) use in that process

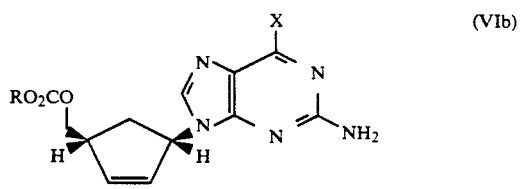

wherein X is chloro, bromo or iodo and R is $(C_{1-6})$ alkyl.

2 Claims, No Drawings

CARBONATE INTERMEDIATES FOR THE SYNTHESIS OF PURINE SUBSTITUTED CYCLOPENTENE DERIVATIVES

This is a division of U.S. Ser. No. 07/505,809, filed Apr. 6, 1990 which is U.S. Pat. No. 5,126,452.

This invention relates to a new process for preparing certain optically active purine substituted cyclopentene derivatives and novel intermediates used in this process. In particular, the invention concerns the synthesis of the 1R-cis isomer of carbovir, (1R-cis)-2-amino-1,9-dihydro-9-[4-(hydroxymethyl) 2-cyclopenten-1-yl]-6H-purin-6-one, an antiviral agent.

BACKGROUND OF THE INVENTION

The compound of formula (I):

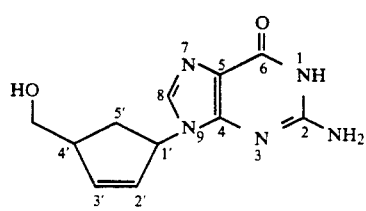

has two optically-active or "chiral" centers, i.e., at the 1' and 4' positions, each of which can exhibit an "R" or an "S" stereo configuration. As will be appreciated by those skilled in this art, a molecule of the compound of formula (I) exists as one of four possible isomers. The concept of stereo configuration and the associated conventions of stereochemistry are explained in essentially all standard tests on organic chemistry, for example, see Mar., J., *Advanced Organic Chemistry*, 3d. Ed., Chap. 4, John Wiley & Sons, N.Y. (1985).

In the compound of formula (I), there are two isomeric pairs each consisting of two enantiomers (isomers which are mirror images of each other). The isomeric pairs are referred to as either "cis" (same side) or "trans" (opposite sides) with respect to the relationship of the non-hydrogen ring substituents attached to the chiral centers. The isomers may be named by specifying the absolute configuration at each chiral center, e.g., 1R, 4S, or prefixing the compound name with the absolute configuration of one of the chiral centers followed by the "cis" or "trans" designation, i.e., 1R-cis, 1R-trans, 1S-cis and 1S-trans.

The cis form of formula (I) is depicted below as formula (II):

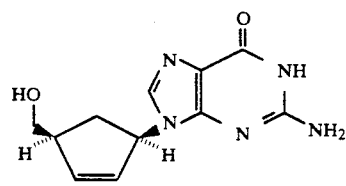

and is meant to represent both cis enantiomers. Thus, the convention of both the 1' and 4' bonds being bold faced is meant to include the enantiomers where the bonds are cis, whether out of the plane of the page or into it. The racemic mixture (equal mixture) of both the 1R-cis and 1S-cis enantiomers of the compound of formula (II) is known as carbovir or (+/−)-carbovir. While racemic carbovir has been reported as having good activity against human immunodeficiency virus (HIV) associated with acquired immune deficiency syndrome (AIDS), the 1R-cis enantiomer of carbovir, also known as (−)-carbovir, (hereinafter these terms are used interchangeably) has been found to have potent activity against this virus (see Vince, R., et al, *Biochem. Biophys. Res. Commun.*, 156 (2), 1046 (1988). In view of the high activity of the 1R-cis enantiomer, it is particularly advantageous to have an efficient method for the synthesis of this enantiomer from relatively inexpensive starting materials.

In view of its guanine moiety, (−)-carbovir exist in two tautomeric forms. For simplicity, herein (−)-carbovir is depicted in the keto form as shown in formula (II), it being understood that it also is represented as the enol form in some publications.

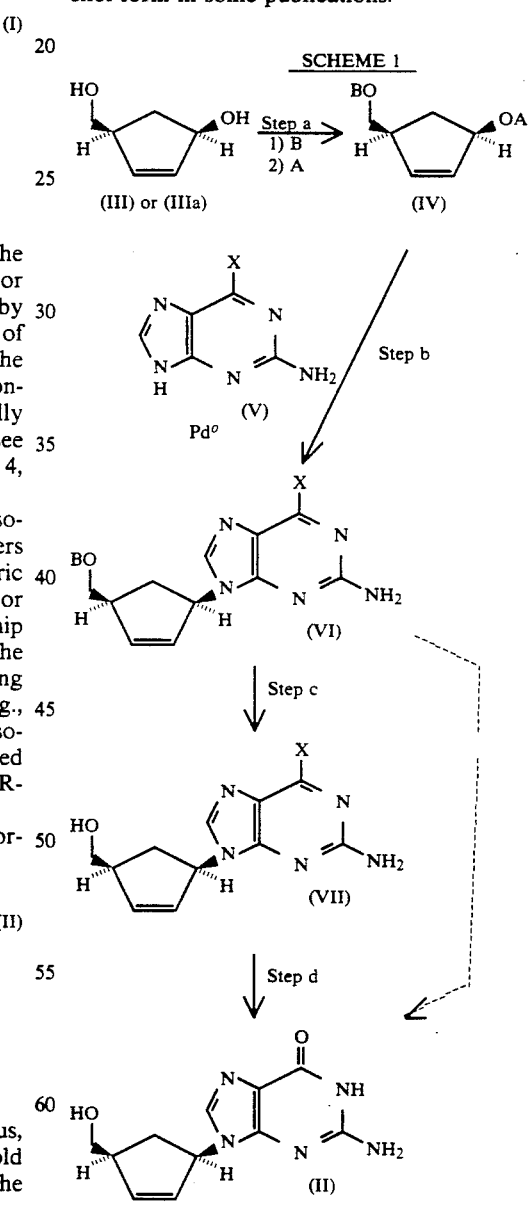

A = Activating group
B = Blocking group
X = Chloro, Bromo or Iodo

SUMMARY OF THE INVENTION

We have now found a novel, efficient method for preparing the 1R-cis enantiomer of carbovir, i.e. (−)-carbovir, starting with cis-4-hydroxymethyl-2-cyclopenten-1-ol. In particular, the present invention provides processes for the synthesis of (−)-carbovir including steps shown in Scheme 1; i.e. (a) protecting the primary hydroxymethyl group of cis-4-hydroxymethyl-2-cyclopenten-1-ol (the compound of formula (III) or its 1R-cis enantiomer, (IIIa)) by the use of the blocking groups, B, recognized in the art as suitable for protecting a primary hydroxymethyl group during palladium catalyzed displacement reactions, and activating the secondary allylic hydroxy group of (III) or its enantiomer, (IIIa), by the use of activating groups, A, recognized in the art as suitable for activating secondary allylic hydroxy groups for palladium catalyzed displacement reactions to yield a compound of formula (IV), (b) reacting (IV) with a compound of formula (V) in the presence of a Pd(O) complex to yield the compounds of formula (VI), (c) removing of the blocking group to yield a compound of formula (VII) or in some cases a compound of formula (II) directly as shown in step (c'), and finally (d) converting the chloro, bromo or iodo group of a compound of formula (VII) to a keto group to yield (−)-carbovir, the compound of formula (II). The distribution of the two enantiomers of carbovir may be controlled by the distribution of enantiomers of the starting material of formula (III) or (IIIa). The distribution may also be controlled by selection of the reagents and reaction conditions for step (d), as described by Vince, et al., U.K. Patent Application No. A and as shown in Scheme 2 below:

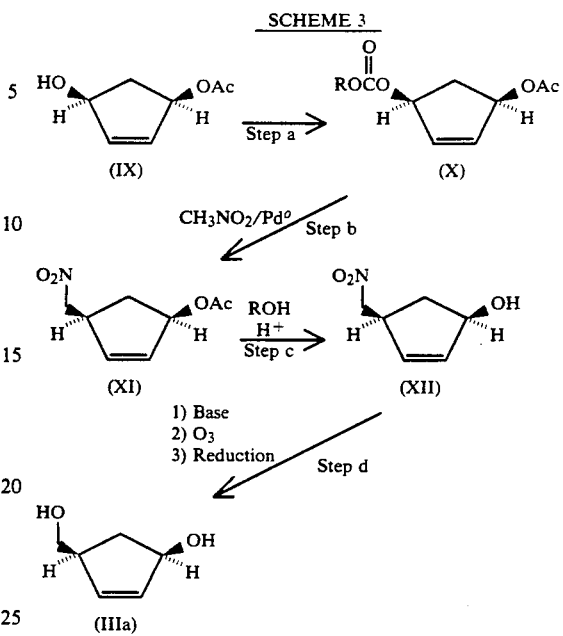

Ac = Alkanoyl
R = $(C_{1-6})$alkyl

Scheme 3 depicts the process for the synthesis of the compound of formula (III) or in particular, (IIIa), i.e., (a) alkoxycarbonylating a compound of formula (IX) where Ac is $(C_{1-6})$ alkanoyl which is in the (1S-cis) configuration with a $(C_{1-14\ 6})$ alkoxycarbonylating agent to yield a compound of formula (X), (b) reacting a compound of formula (X) with nitromethane in the presence of a Pd(0) complex to yield compound of formula (XI), (c) hydrolysis of the compound of formula (XI) to generate the compound of formula (XII) and (d) conversion of the nitro group of the compound of formula (XII) to give cis-4-hydroxymethyl-2-cyclopenten-1-ol, the compound of formula (III). It will be observed that the (1R-cis) enantiomer of the compound of formula (III), i.e., the compound of formula (IIIa) can also be made by this procedure by starting with the corresponding enantiomer of the compound of formula (IX), i.e., the (1S-cis) enantiomer or resolving an enan-

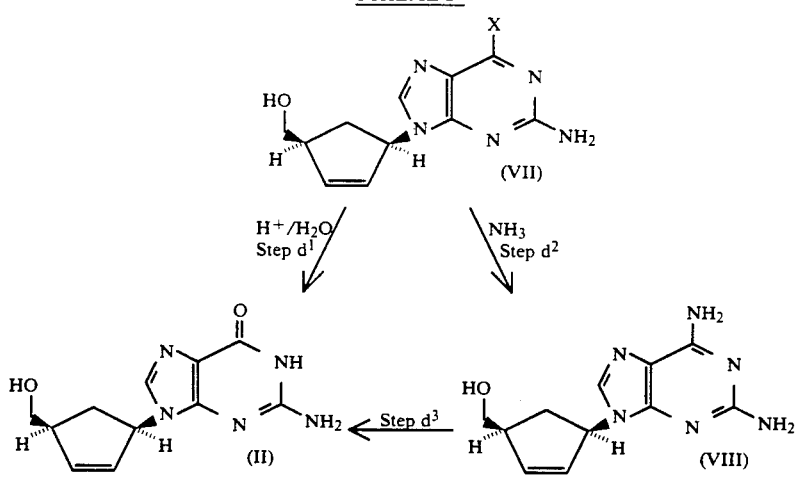

Scheme 2 depicts step (d) of Scheme 1 in greater detail. If formula (VII) is racemic, one may enrich the product (II) in the desired enantiomer by using intermediate compound of (VIII). In turn, the compound of formula (VIII) is made by reacting (VII) with ammonia in step ($d^2$). The compound of formula (VII) is then incubated with the enzyme adenosine deaminase in step ($d^3$) to selectively yield (−) carbovir.

tiomeric mixture of the compounds of formulas (X), (XI) or (XII).

Further embodiments of the present invention are certain novel intermediates derived in Schemes 1 and 4, and the methods for preparing these intermediates.

DETAILED DESCRIPTION OF THE INVENTION

The process shown in Scheme 1 may conveniently be carried out by either route ($b^1$-$c^1$) or ($b^2$-$c^2$) shown in Scheme 4 for protecting the primary hydroxymethyl group and activating the secondary hydroxy group of the compound of formula (III) or (IIIa). The protecting groups, also known as "blocking" groups, added in step (a) may be any such groups recognized in the art of organic chemistry as suitable for protecting primary hydroxymethyl groups under the displacent conditions of step (b), and removable at the conclusion of step (b). Examples of suitable blocking groups include those reported by T. W. Green in *Protecting Groups in Organic Synthesis*, Chapter 2, page 10, J. Wiley and Sons, N.Y., 1981. Typically primary hydroxymethyl groups are blocked by the formation of sterically hindered ethers, e.g., triphenylmethyl ether or ($C_{1-4}$) alkyl esters of carbonic acids, e.g., methyl carbonate.

The activating group may be any group suitable for activating a secondary allylic hydroxy group for palladium catalyzed displacement reactions. Examples of suitable secondary hydroxy groups activating groups include those reported by J. Tsuji, *Tetrahedron*, 42, 4361 (1986). . Typical activating groups include carbonates, ($C_{1-6}$) alkanoic acid esters, aryloic acid esters aralkanoic acid esters, allyl ethers, aryloxy ethers and halo groups, e.g. chloro.

In some cases a single groups can serve both the blocking and activating functions and be used on each of the hydroxy groups, e.g., methyl carbonate.

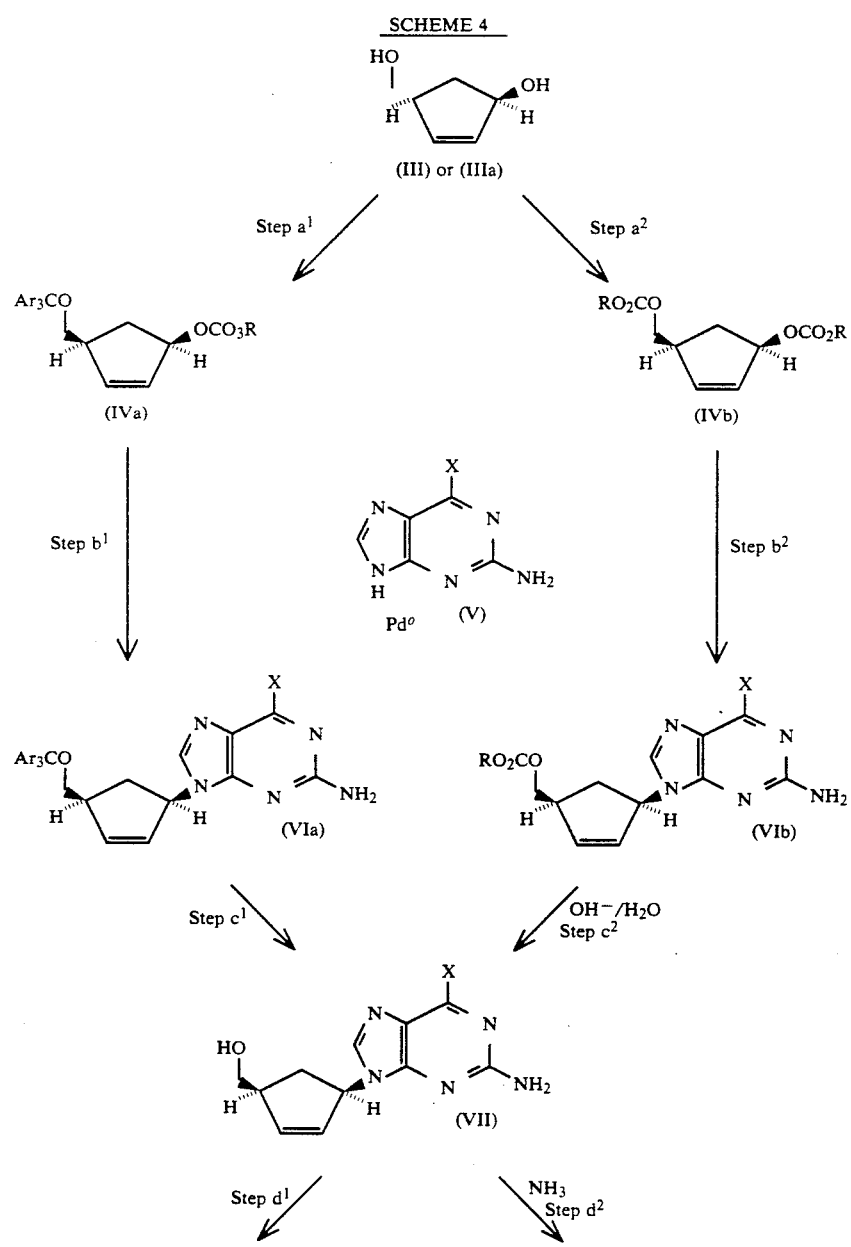

SCHEME 4

-continued

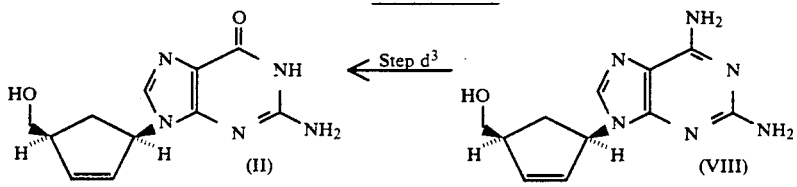

X = Br, Cl, or I
Ar = substituted or unsubstituted phenyl
R = (C$_{1-6}$) alkyl

Step (a$^1$) of Scheme 4 may be effected by reacting the compound of formula (III) with a triarylmethyl halide (wherein aryl is a substituted or unsubstituted phenyl group), for example, triphenylmethyl chloride in a temperature range from about 15° C. to about 30° C., followed by treatment with an (C$_{1-6}$) alkyl haloformate, for example n-butyl chloroformate, in a temperature range from about −5 to about 10° C. Step (a$^2$) can be accomplished by reacting the compound of formula (III) with a di(C$_{1-6}$)alkyl pyrocarbonate, for example, dimethyl pyrocarbonate in the presence of a tertiary amine in a temperature range of from about −5° to about 10° C.

In Scheme 4, steps a$^1$ and a$^2$ may also be carried out with the 1R-cis enantiomer of (III), i.e., the compound of formula (IIIa), or the racemic products of formulas (IVa) and (IVb) may be resolved before proceeding with steps b$^1$ or b$^2$. In addition, a resolution of enantiomers from a racemate may be carried out at one or more other points, such as on the compounds of formulas (VIa), (VIb) or (VII) before proceeding with the next step. The various aspects of the invention cover all such modifications and herein are meant, unless otherwise indicated, to be inclusive of the reaction of an individual enantiomer.

Steps (b$^1$) or (b$^2$) of Scheme 4 are conveniently executed by reacting the compounds of formulas (IVa) or (IVb) with a compound of formula (V) in the presence of a Pd(O) complex, for example, tetrakis(triphenylphosphine)palladium(O) in a temperature range from about 15° C. to about 80° C. in an aprotic solvent, e.g., tetrahydrofuran or dimethylsulfoxide, in an analogous manner to that taught by B. M. Trost in *J. Am. Chem. Soc.*, 110, 621 (1988) to yield the compounds of formulas (VIa) and (VIb) respectively. For the compound of formula (V), X is chloro, bromo or iodo, e.g., 2-amino-6-chloropurine which is commercially available.

Steps (c$^1$) or (c$^2$) of Scheme 4, the removal of the hydroxy protecting groups of the compounds of formulas (VIa) and (VIb), yield a compound of formula (VII) and may be performed by any suitable method of the art for removal of these protecting groups. For example, a compound of formula (VIa) can be treated with an alkanoic acid, e.g. acetic acid, and water at ambient temperatures (about 15-30° C.) Further, a compound of formula (VIb) can be treated with an aqueous hydroxide, e.g., aqueous sodium hydroxide, at temperatures from about 15° C. to about 100° C.

Step (d) of Scheme 1 constitutes conversion of a compound of formula (VII) to the 1R-cis enantiomer of the compound of formula (II), i.e., (−)-carbovir. This step may be carried out by reacting the compound of formula (VII) sequentially with i) a source of ammonia followed by ii) an enzymatic hydrolysis agent at ambient temperature which selectively yields (−)-carbovir as shown in steps (d$^2$) and (d$^3$) of Scheme 2 and 4. For example, step (d$^2$) can be accomplished by the reaction of (VII) with liquid ammonia at a molar ratio of about 1:10 to about 1:100 in a sealed bomb at a pressure of about 1 to 100 atm. at a temperature of from about 60° C. to about 90° C. Step (d$^3$) may be carried out by incubation of (VIII) with adenosine deaminase in a buffered aqueous solution at ambient temperature.

Alternatively, the compound of formula (VII) can be converted directly to the compound of formula (II) by hydrolysis as shown in step (d1) in Schemes 2 and 4. For example, (VII) can be treated with aqueous acid or base at elevated temperatures, e.g., hydrochloric acid or aqueous sodium hydroxide (see R. Vince and M. Hua, *J. Med. Chem.*, 33, 17-21 (1990) for a similar reaction) at from about 15° C. to about 100° C. It will be recognized that step (d$^1$) is not enantioselective and optically pure (−)-carbovir can be obtained only if (VII) is the optically pure, corresponding enantiomer. Thus, if (VII) is racemic, then step d$^1$ yields (+/−)-carbovir, (II).

The racemic compound of formula (III) may be prepared by the method of J. J. S. Bajorek, et al., reported in *J. Chem. Soc., Perkin Trans.* 1, 1243-1245 (1974). However, the 1R-cis enantiomer of the compound of formula (III), i.e., the compound of formula (IIIa), may be prepared by the method shown in Scheme 3 and described hereinbelow. A compound of formula (IX) which is in a stereo configuration which corresponds to that of the compound of formula (IIIa), i.e., (1S-cis)-2-cyclopenten-1,4-diol 4-acetate, is treated in step (a) with an (C$_{1-6}$) alkoxycarbonylating agent, e.g., dimethyl pyrocarbonate in the presence of a tertiary amine base, e.g., 4-(dimethylamino)pyridine, in a suitable anhydrous, aprotic solvent, e.g., tetrahydrofuran, in a temperature range from about 0° C. to about 30° C. The starting material, a compound of formula (IX), may be purchased commercially, or may be prepared according to the method taught by T. Sugai and K. Mori, *Synthesis*, 19–22, (1988).

In step (b) of Scheme 3 a compound of formula (X) is reacted with nitromethane in the presence of a Pd(O) complex, e.g., tris(dibenzylideneacetone)dipalladium(chloroform), and a trialkyl phosphite, e.g. triisopropyl phosphite, at a temperature in the range of about −5° C. to about 10° C., preferably about 0° C. to yield the compound of formula (XI). In step (c), the ester portion of the compound of formula (XI) may be converted to a hydroxy group by hydrolysis using any suitable method of the art to give the compound of formula (XII). Examples of hydrolysis conditions include p-toluenesulphonic acid monohydrate in a molar ratio to (XI) from about 1:1.8 to about 1:2.3 in methanol at about 20° C. for about 18 hours.

Finally in step (d) of Scheme 3 the compound of formula (IIIa) may be obtained by sequentially reacting the compound of formula (XII) with a suitable strong base, e.g. sodium methoxide in methanol; with ozone and with a reducing agent to yield the desired hydroxy function. An alkali metal or alkaline earth metal hydride, e.g. sodium borohydride, may serve as the reducing agent.

It should be noted that either of the cis enantiomers or a combination thereof for the compounds of formulas (X), (XI), (XII) and (III) can be prepared by the method of Scheme 3 by selection of the stereo configuration of the starting material, the compound of formula (IX). For example, the (b 1S-cis) enantiomer of the compound of formula (III), if desired, may be prepared by starting with a compound of formula (IX) in the (1R-cis) rather than the (1S cis) configuration.

The novel intermediate compounds disclosed in Schemes 1 and 4, which constitute an additional aspect of this invention are those of formulas (IVa), (IVb), (VIa) and (VIb) all of which include both cis enantiomers or mixtures thereof, including racemates.

Particular compounds of formulas (IVa), (IVb), (VIa) and (VIb), respectively, are:

a) cis-4-((Triphenylmethoxy)methyl)-2-cyclopenten-1-ol-1-(n-butylcabonate);
b) cis-4-Hydroxymethyl-2-cyclopenten-1-ol 1,4-bis-(methylcarbonate);
c) cis-2-Amino-6-chloro-9-(4-(hydroxymethyl)-2-cyclopenten-1 yl)-9H-purine triphenylmethyl ether and
d) cis-2-Amino-6-chloro-9-(4-(hydroxymethyl)-2-cyclopenten -1-yl)-9H-purine methylcarbonate.

The following examples illustrate aspects of this invention but should not be construed as limitations thereto. As used herein the symbols and conventions used in these examples are consistent with those used in the contemporary chemical literature, for example, the *Journal of the American Chemical Society*.

EXAMPLE 1

Cis-4-Hydroxymethyl-2-cyclopenten-1-ol (III)

Following the general procedure reported by J. J. S. Bajorek, R. Battaglia, G. Pratt, and J. K. Sutherland (*J. Chem. Soc., Perkin Trans.* 1 (1974) 1243–1245), a suspension of paraformaldhyde (42.7g, 1.42 mol) in 96% formic acid (160 mL, 4.27 mol) is heated to reflux to solubilize the paraformaldehyde. Once the paraformaldehyde is dissolved, the solution is cooled to 0° C. To the resulting hazy solution is added freshly cracked cyclopentadiene (25 mL, 0.406 mol) dropwise while the reaction temperature is maintained between 0° C. and +2° C. under a nitrogen atmosphere.

After stirring the reaction mixture at 0° C. for 2 hours, the ice bath is removed and the reaction mixture is stirred at room temperature for up to 72 hours. The resultant black solution is cooled to −5° C. and 10N sodium hydroxide (450 mL, 4.50 mol) is added to adjust the pH to 14. The reaction temperature is kept between −5° C. and 5° C. throughout the sodium hydroxide addition. After the addition is complete, the reaction mixture is stirred at 0° C. for 20 minutes, and the resultant dark brown oily solution is filtered through a diatomaceous earth pad. The pH of the amber aqueous solution is adjusted to pH 5.5 by the addition of 12 N hydrochloric acid. A cooling bath is required to keep the temperature of the reaction mixture below 25° C.

Acetonitrile is added and the solution is concentrated in vacuo to azeotropically remove water. As the water is removed, large amounts of salts precipitate from the solution. The salts are filtered and the salt cake is washed with acetonitrile (2×100 mL).

The filtrate is concentrated in vacuo to a brown oil and the flask containing the brown oil is equipped with a short path distillation apparatus. The flask is evacuated and lowered into a pre-heated oil bath at 160° C. The desired diol mixture is distilled at 110° C. (0.25 mm Hg) as a clear water-white oil and is part of a mixture of products. The crude product is further purified by flash chromatography by using a ratio of 1 g product to 100 g silica gel (32–63μm) and eluting with 10% methanol/methylene chloride. The desired cis-4-hydroxy-methyl-2-cyclopenten-1-ol (Rf=0.54), and the trans-4-hydroxymethyl-2-cyclopenten-1ol (Rf=0.49) are recovered separately. The desired cis-4-hydroxymethyl-2-cyclopenten-1-ol exhibits the following physical data: 1R (thin film, cm$^{-1}$): 3300 (br), 3049 (w), 2920°–2870 (s), 1645 (w), 1030 (s), 1000 (s), 730 (m); and MS (CI) m/z =97 ($C_6H_9O+$), 79 ($C_6H_7+$).

EXAMPLE 2 cis-4-Hydroxymethyl-2-cyclopenten-1-ol 1,4 bis-(Methyl carbonate) (IVb)

To a dry 10 mL round-bottom flask containing a nitrogen atmosphere is added cis-4-hydroxymethyl-2-cyclopenten-1-ol as prepared in Example 1 (0.218g, 1.91 mmol), 4-(dimethylamino)pyridine (0.024 g, 0.196 mmol) and anhydrous tetrahydrofuran (2 mL). The resultant solution is cooled to 0° C. and dimethyl pyrocarbonate (2 mL, 20.7 mmol) is added dropwise. After 15 minutes, the ice bath is removed and the reaction mixture is stirred overnight.

The reaction mixture is concentrated on a rotary evaporator with a water aspirator to an oil which is purified by flash chromatography on silica gel (32–63μm) by eluting with 20% ethyl acetate/hexane. The fractions containing the desired product (Rf=0.46, 20% ethyl acetate/hexane) are combined and are concentrated on a rotary evaporator to give cis-4-hydroxymethyl-2-cyclopenten-1-ol 1,4 bis-(methylcarbonate) as a clear oil which exhibits the following physical data: 1R (thin film, cm$^{-1}$) 2965 (s), 2830 (m) 1750 (s), 1620 (w), 1590 (w), 1450 (s), 1335 (s), 1260 (s), 990 (s), 945 (s), 800 (s); and MS (CI, m/z): 231 (M+1); 155 ($C_8H_{11}O_3+$).

EXAMPLE 3 cis-2-Amino-6-chloro-9-[4-(hydroxymethyl)-2-cyclopenten-1yl]-9H-purine Methylcarbonate (VIb)

To a 5 mL round-bottom flask containing a nitrogen atmosphere is added 2-amino-6-chloropurine (0.081 g, 0.478 mmol), tetrakis(triphenylphosphine)palladium (0.01 g, 0.0086 mmol), and dimethyl sulfoxide (1 mL). To this solution is added a solution of cis-4-hydroxymethyl-2-cyclopenten-1-ol 1,4 bis-(methylcarbonate) (0.10 g, 0.435 mmol) as prepared in Example 2 and anhydrous tetrahydrofuran (1 mL) and the reaction mixture is stirred at 25° C. After one hour the reaction mixture is concentrated in vacuo at 0.25 mm Hg to a yellow solid. The solid is purified by flash chromatography on silica gel (32–63μm) by eluting with 10% acetonitrile/ethyl acetate. The fractions containing the desired product (Rf=0.65) are combined and are concentrated in vacuo on a rotary evaporator to give cis-2-amino-6-chloro-9-[4-(hydroxymethyl)-2-cyclopenten-1- yl]-9H-purine methylcarbonate as a white solid which exhibits the following physical data: 1R (CHCl$_3$, cm$^{-1}$) 3520 (w), 3420 (w), 3010 (w), 1750 (s), 1610 (s), 1565 (s), 1275 (s), MS(FAB): m/z 324 (M+1): contains 1 chlorine atom; UV (EtOH), nm $_{max}$=310, 225, 250 $_{min}$=265; and mp 119°–121° C.

EXAMPLE 4 cis-2-Amino-1,9-dihydro-9-4-(hydroxymethyl)-2-cyclopenten-1-11-6H-purine-6-one (II)

To a 5 mL round-bottom flask equipped with a reflux condenser is added cis-2-amino-6-chloro-9-[4-(hydroxymethyl)-2-cyclopenten-1-yl]-9H-purine methylcarbonate as prepared in Example 3 (10 mg, 0.031 mmol), sodium hydroxide (2.5 mg, 0.062 mmol), and deionized water (1 mL). The resultant heterogeneous mixture is heated at 75° C. for 12 hours. The reaction mixture becomes a pale amber solution which is filtered hot through a bed of diatomaceous earth. The pH of the filtrate is adjusted to pH 7 with 1N hydrochloric acid. Acetonitrile is added and the solution is concentrated in vacuo to a solid via azeotropic removal of water. The solid is tritriated with 2 mL of methanol and the solution is filtered. The filtrate is concentrated in vacuo to give cis-2-amino-1,9-dihydro-9-[4-(hydroxymethyl)-2-cyclopenten-1-yl ]-6-purine-6-one as a white solid which exhibits the following physical data: 1R (nujol mull, cm$^{-1}$) 3500–3600 (br, m), 1725 (m), 1630 (s), 1605 (s); UV (EtOH, nm) max =275, 255; min =225; and mp 268°–270° C.

EXAMPLE 5 cis-4-[(Triphenylmethoxy)methyl]-2-cyclopenten-1-ol (Precursor to IVa)

A mixture of cis- and trans-4-hydroxymethyl-2-cyclopenten-1ols [(III) and the trans-isomer](4.57 g, 40.1 mmol) is dissolved in 55 mL of anhydrous pyridine and 12.33 g (44.2 mmol) of triphenylmethyl chloride is added. The mixture is stirred at room temperature under a nitrogen atmosphere for 65 hours. The mixture is poured into 175 mL of ice water and extracted with 2×250 mL of ethyl acetate. The combined organic extracts are successively washed with cold 1N hydrochloric acid, water, and saturated aqueous sodium bicarbonate solution.

The organic phase is dried over anhydrous magnesium sulfate, filtered, and evaporated to dryness in vacuo to yield 16.8 g of a brown syrup. This material is dissolved in a small amount of ethyl acetate, evaporated onto a small amount of silica gel, and then flash column chromatographed on a 200 g column of 230–400 mesh silica gel. Elution with a gradient of hexane/ethyl acetate starting at a ratio of 9:1 and gradually increasing to 3:1 afforded 3.98 g of cis-4-[(triphenylmethoxy)methyl]-2-cyclopenten-1-ol which exhibits the following physical data: mp 110°–113° C.; Anal. Calcd. for C$_{25}$H$_{24}$O$_2$: C:84.24; H:6.79. Found C:83.99; H:6.69. A total of 2.50 g of the corresponding trans-isomer, mp 94°–96° C.,; and Anal. Calcd. for C$_{25}$H$_{24}$O$_2$: 84.24; H:6.79. Found: C:84.04; H:6.65, is also obtained.

EXAMPLE 6 cis-4-(Triphenylmethoxy)methyl[-2-cyclopenten-1-ol 1-(nButylcarbonate) (IVa)

Cis-4-[(triphenylmethoxy)methyl]-2-cyclopenten-1-ol as prepared in Example 5 (0.253 g, 0.711 mmol) is dissolved in 10 mL of anhydrous methylene chloride under a nitrogen atmosphere, then cooled to 0° C. in an ice-water bath. To this solution is added 0.30 mL (3.71 mmol) of anhydrous pyridine, followed shortly thereafter by 0.21 mL (1.65 mmol) of n-butyl chloroformate. The solution is stirred at 0° C. for 1.5 hours at which time the reaction is complete. The solution is treated with water to destroy the excess n-butyl chloroformate. The mixture is partioned and the organic phase is washed with water and saturated aqueous sodium bicarbonate solution. The organic layer is dried over anhydrous magnesium sulfate, filtered and evaporated to dryness. The resulting clear oil is dissolved in 100 mL of toluene and evaporated to dryness to remove traces of pyridine and yield 0.326 g of cis-4-[(triphenyl- methoxy)methyl]-2-cyclopenten-1-ol 1-(n-butylcarbonate). TLC: Rf =0.65 [ethyl acetate(1): hexane(5)].

EXAMPLE 7 cis-2-Amino-6-chloro-9-[4-(hydroxymethyl)-2-cyclopenten1-yl]-9H-purine Triphenylmethyl Ether (VIa)

Tetrakis(triphenylphosphine)palladium (0) (44.4 mg, 5.4 mol per cent), and 0.133 g (0.785 mmol) of 2-amino-6-chloropurine is dissolved in 15 mL of anhydrous tetrahydrofuran and 15 mL of anhydrous dimethyl sulfoxide under a nitrogen atmosphere. Cis-4-[(triphenylmethoxy)methyl-2-cyclopenten-1-ol 1-(n-butylcarbonate) as prepared in Example 6 (0.326 g, 0.71 mmol) in 15 mL of anhydrous tetrahydrofuran is added and the solution is heated to 60° C. for 2.5 hours. The solvent is removed in vacuo to yield a brown syrup. Flash column chromatography on silica gel with a gradient of hexane-ethyl acetate starting from 3:1 and gradually increasing to 1:1 give 0.104 g of cis-2-amino-6-chloro-9-[4 (hydroxymethyl)-2-cyclopenten-1-yl]-9H-purine triphenymethyl ether; m.p. 86°–90° C. (dec), shrivels 72°–80° C. and TLC: Rf=0.33 [ethyl acetate (1), hexane (1)].

EXAMPLE 8 cis-2-Amino-6-chloro-9-[4-(hydroxymethyl)-2-cyclopenten-1-yl]-9H-purine (VII)

Cis-2-amino-6-chloro-9-[4-(hydroxymethyl)-2-cyclopenten-1-yl]-9H-purine triphenylmethyl ether as prepared in Example 7 (0.183 g 0.36 mmol) is dissolved in 22 mL of 4:1 acetic acid:water (80% acetic acid) and stirred under a nitrogen atmosphere at room temperature for 26 hours. The reaction mixture is evaporated in vacuo and the residue is dissolved in successive 100 mL portions of 2-propanol which are evaporated to dryness. The semisolid material is flash column chromatographed on 230–400 mesh silica gel using 24:1 chloroform-methanol as eluant to yield 0.0566 g of cis-2-amino-6-chloro-9-[4-(hydroxymethyl)-2-cyclopenten-1-yl]-9H-purine, m.p. 138°–140° C.(dec), shrivels at 125°–130° C.; TLC: Rf =0.25 [MeOH(1):CHCl$_3$(9)]. This material is converted into cis-2-amino-1,9-dihydro-9-[4-(hydroxymethyl)-2-cyclopenten-1-yl]-6H-purin-6-one (II) according to U.K. patent application number 221720 A and R. Vince and M. Hua, J. Med. Chem., 33, 17–21 (1990).

EXAMPLE 9

(1S-cis)-2-Cyclopentene-1,4-diol 1-(Methylcarbonate) 4Acetate (X)

To a 10 mL round-bottom flask containing a nitrogen atmosphere is added commercially available (1S-cis)-2- cyclopenten-1,4-diol 4-acetate of formula (IX) (0.2 g, 1.41 mmol) (Fluka Chemical Corporation, Ronkonkoma, NY), 4-(dimethylamino)pyridine (0.017 g, 0.14 mmol) and anhydrous tetrahydrofuran (2 mL). The resulting solution is cooled to 0° C. and methyl pyrocarbonate (1.5 mL) is added dropwise over two minutes. After stirring the reaction mixture at 0° C. for 30 minutes, the ice bath is removed and the reaction mixture is stirred overnight at room temperature. The reaction mixture is then concentrated to an oil in vacuo and the oil is purified by flash chromatography (32μm-63μm) by eluting with 20% ethyl acetate/hexane. The fractions containing the desired product are combined (Rf=0.5) and are concentrated in vacuo to give (1S-cis)-2-cyclopentene-1,4-diol 1-(methylcarbonate) 4-acetate as a clear oil which exhibited the following physical data: IR (thin film, cm$^{-1}$) 2970 (s), 1750 (s), 1590 (w), 1450 (s), 1385 (s), 1350 (s), 1080 (s), 1030 (s), 985 (s), 960 (s), 800 (s); MS(CI) =m/z 201 [M+1], 141 [$C_7H_9O_3$+], 125 [$C_6H_5O_3$+]; and $[\alpha]D^{20}$= −2.6° (c=0.34, CHCl$_3$).

EXAMPLE 10

(1R-cis) 4-Nitromethyl-2-cyclopentene 1-Acetate (XI)

To a 10 mL round-bottom flask containing a nitrogen atmosphere is added tris(dibenzylideneacetone)dipalladium(chloroform) [Pd$_2$(DBA)$_3$CHCl$_3$] (6.5 mg, 6.25μmol), triisopropyl phosphite (12 uL, 46 μmol) and nitromethane (2 mL). This heterogeneous catalyst mixture is stirred until the color changed from purple to a pale yellow solution. At this point, the solution is cooled to 0° C. and a solution of (1S-cis)-2-cyclopentene-1,4-diol 1-(methylcarbonate) 4-acetate in nitromethane (1 mL) as prepared in Example 9 and tetrahydrofuran (1 mL) is added dropwise over one minute. After one hour, the crude reaction mixture is filtered through 1¼" pad of silica gel and the silica gel pad was eluted with ethyl acetate. The filtrate is concentrated to an oil in vacuo and the oil is purified by flash chromatography on slicia gel (32μm-63μm) by eluting with 20% ethyl acetate/hexane. The fractions which contain the product (Rf=0.45) are combined and concentrated in vacuo to give (1R-cis)-4-nitromethyl-2-cyclopentene 1-acetate as a clear oil which exhibited the following physical data: IR (thin film, om $^{-1}$) 1735 (s), 1550 (s), 1430 (m) 1380 (s), 1375 (s), 1195 (s), 1080 (m), 1020 (s); and MS (CI) m/z =186 (M+1), 168 [$C_8H_{10}NO_3$+], 139 [$C_8H_{11}O_2$+], 126[$C_6H_8NO_2$+].

EXAMPLE 11

(1-cis)-4-Nitromethyl-2-cyclopenten-1-ol (XII)

To a 5 mL round-bottom flask is added at room temperature p-toluenesulphonic acid monohydrate (0.01 g, 0.053 mmol), methanol (8 mL) and (1R-cis)-4-nitromethyl-2-cyclopentene 1-acetate as prepared in Example 10 (0.20 g, 1.1 mmol) and the resulting solution is stirred overnight. The crude reaction mixture is loaded on a silica column (32μm-63μm) and purified by flash chromatography by eluting with 20% ethyl acetate/hexane. The fractions containing the product (Rf=0.3) are combined and are concentrated in vacuo to give (1R-cis)-4-nitromethyl-2-cyclopenten-1-ol as a clear oil which exhibited the following physical data: MS(CI) m/z =126 [$C_6H_8NO_2$+, Loss of H$_2$O followed by rapid protonation]; and $[\alpha]D_{20}$= +4.8° (c=0.16, CHCl$_3$).

EXAMPLE 12

(1R-cis)-4-Hydroxymethyl-2-cyclopenten-1-ol (IIIa)

To a two-neck 100 mL round-bottom flask containing a nitrogen atmosphere and equipped with a Dry Ice-acetone jacketed dropping funnel is added anhydrous methanol (2.5 mL) and (1R-cis)-4-nitromethyl-2-cyclopenten-1-ol as prepared in Example 11 (0.05 g, 0.27 mmol). The resultant solution is cooled to 0° C. and sodium methoxide (25% w/w in methanol, 0.080 mL) is added. The solution is stirred at 0° C. for 15 minutes before cooling to −78° C. In a separate flask, methylene chloride (50 ml) is cooled to −78° C. and saturated with ozone as is indicated by a persistent blue color. A 20 mL portion of the saturated ozone solution is removed and is added dropwise via the Dry Ice-acetone cooled addition funnel to the (1R-cis)-4-nitromethyl-2-cyclopenten-1-ol solution. After 10 minutes, sodium borohydride (0.02 g, 0.54 mmol) is added and the reaction stirred for 10 minutes at −78° C.

The reaction mixture is then allowed to warm slowly to room temperature over 10 minutes and subsequently stirred at room temperature for 15 minutes. Deionized water (0.5 mL) is added and the reaction mixture is stirred at room temperature for an additional 15 minutes before the reaction mixture is concentrated to an oil in vacuo. The oil is purified by flash chromatography on silica gel (32–63 μm) by eluting with 100% ethyl acetate. The fractions containing the product (Rf=0.5) are combined and are concentrated in vacuo to give (1R-cis)-4-hydroxymethyl-2-cyclopenten-1-ol. The starting material (1R-cis)-4-nitromethyl-2-cyclopenten-1-ol is also recovered (Rf=0.75). The desired (1R-cis)-4-hydroxymethyl-2-cyclopenten-1-ol exhibited the following physical data: IR (thin film, cm$^{-1}$): 3300 (br), 3049 (w), 2920–2870 (s), 1645 (w); and $\alpha[D^{20}$= −36° (c=0.07, CHCl$_3$).

EXAMPLE 13 cis-2,6-Diamino-9-4-(hydroxymethyl)-2-cyclopenten-1-yl]-9H-purine (VIII)

In a chilled 120 mL Teflon lined Parr bomb is placed 45.0 g (0.170 mol) of cis-2-amino-6-chloro-9-[4-(hydroxymethyl)-2-cyclopenten-1-yl]-9H-purine as prepared in Example 8 and 85 mL of liquid ammonia. The Parr bomb is reassembled and placed in an oil bath at 75-80° C. The mixture is heated at 75°-80° C. for forty-eight hours in a secure hood. The reaction is cooled and checked for completion by thin layer chromatography. The ammonia is allowed to evaporate and the solids are dissolved in 1.2 L of methanol.

The solution is filtered to remove solid residual ammonium chloride and the residue is washed with 2×50mL =100mL of methanol. The washes and filtrates are combined and concentrated at 35° C. (50 mm) to a volume of about 300 mL to induce crystallization. Then 400 mL of 2-propanol are added to the slurry and this mixture is stored in a freezer overnight at −° C. The solid product is isolated by vacuum filtration and washed with 2×50 mL =100 mL of 2-propanol. The product is dried in a vacuum oven at 90° C. to constant weight to yield 39.0 g (93%) of white crystalline cis-2,6-diamino-9-[4-(hydroxymethyl)-2-cyclopenten-1-yl]-9H-purine which exhibits mp 178°-180° C.

EXAMPLE 14

(1R-cis)-2-Amino-1,9-dihydro-9-[4-(hydroxy-methyl)-2-cyclopenten-1-yl -6H-purin-6one (II, 1R-cisconfiguration)

In a 2 L, 4-necked round bottomed flask equipped with a glass rod stirrer, a thermometer, a gas inlet tube, and an addition tube with a glass pH electrode is placed 47.8 g (0.194 mol) of cis-2,6-diamino-9-[4-(hydroxymethyl)-2-cyclopenten-1-yl]-9H-purine as prepared in Example 13, and 1.6 L of 0.05 M aqueous potassium phosphate dibasic solution (pH 7.5 buffer). The slurry is heated to 40° C. with stirring to form a homogeneous solution.

Then 31,000 units of adenosine deaminase (Type VIII, from calf intestinal mucosa, Sigma) are added to the solution. The temperature is held at 38±2° C. with a temperature controlled oil bath. The pH is held at pH 7.4–7.8 with a Cole Palmer pH controller attached to a source of 0.5 N aqueous phosphoric acid. Approximately 90 mL of the aqueous phosphoric acid is added during the reaction. The progress of the reaction is monitored by HPLC and slowed considerably as the 50% reaction point was reached at 64 hr. During this time some product precipitated from the reaction mixture. The pH of the slurry is adjusted to pH 9.2 by adding 5 mL of concentrated ammonium hydroxide. The slurry is cooled to 5° C. and stirred for 30 minutes to fully effect product crystallization. The crude product is isolated by filtration and washed with 2×25 mL =50 mL of deionized water at 0°-5° C. The water layer and washes are saved. The crude product is dried in a vacuum oven at 90° C. to constant weight to yield 17.8 g of off-white crystalline solid.

The product is dissolved in 950 mL of deionized water at 90°-95° C. in a 2 L Erlenmeyer flask and 0.5 g of decolorizing carbon is added. The hot solution is filtered through 1½ Celite bed in a steam jacketed Buchner funnel. The Celite bed is washed with 2×50 mL =100 mL of deionized water at 90°-95° C. The colorless solution is allowed to cool to 25±5° C. over a one-hour period to effect crystallization. The resulting slurry is cooled to 0°-5° C. and agitated occasionally for 45 minutes. The product is isolated by vacuum filtration and is washed with 25 mL of deionized water at 0°-5° C. The water layer and washes are saved. The product is dried in a vacuum oven at 80° C. to constant weight to yield 16.5 g (34.5%, 69% of theoretical) of white fluffy solid (1R-cis) -2-amino-1,9-dihydro-9-[4-(hydroxymethyl)-2-cyclopenten-1yl]-6H-purin-6one, i.e. (−)-carbovir: mp 269°-272° C. (dec); $[\alpha]D^{20} = -66.2°$ (c=0.08, CH$_3$OH).

We claim:

1. A compound of formula (VIb)

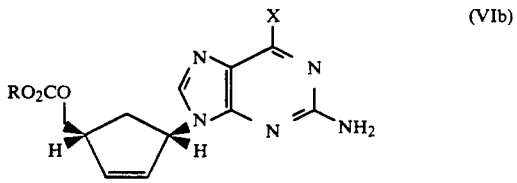

wherein X is chloro, bromo or iodo and R is (C$_{1-6}$) alkyl.

2. The compound of claim 1 which is cis-2-amino-6-chloro-9-[4-(hydroxymethyl)-2-cyclopenten-1-yl]-]-9H-purine methylcarbonate.

* * * * *

UNITED STATES PATENT AND TRADEMARK OFFICE
CERTIFICATE OF CORRECTION

PATENT NO. : 5,241,069

DATED : August 31, 1993

INVENTOR(S) : Vince et al.

It is certified that error appears in the above-identified patent and that said Letters Patent is hereby corrected as shown below:

On title page, item [73] Assignee, should read as follows: --University of Minnesota--.

Column 3, line 33, change "Application No. A" to --Application No. 2217320A--.

Column 4, line 34, change "$(C_{1-14\ 6})$" to --$(C_{1-6})$--.

Column 6, line 12, change "(1986) .. Typical" to --(1986). Typical--.

Column 7, line 43, change "phosphine) palladium" to --phosphine)-palladium--.

Column 8, line 57, change tris(dibenzylideneacetone)dipalladium (-chloroform)" to --tris(dibenzylideneacetone) dipalladium-(chloroform)--.

Column 9, line 13, change "(b 1S-cis)" to --(1S-cis)--.

Column 9, line 40, change "-2-cvclopenten-1-ol" to ---2-cyclopenten-1-ol--.

Column 10, line 18, change "2920°-2870" to --2920-2870--.

Column 10, line 51, change "penten-1yl]-9H-" to --penten-1-yl]-9H---.

Column 11, line 9, change "dihydro-9-4-(hydroxymethyl)-2-cyclo-" to --dihydro-9-[4-(hydroxymethyl)-2-cyclo---.

Column 11, line 10, change "penten-1-11-6H-purine-6-one (II)" to --penten-1-yl]-6H-purine-6-one (II)--.

UNITED STATES PATENT AND TRADEMARK OFFICE
CERTIFICATE OF CORRECTION

PATENT NO. : 5,241,069

DATED : August 31, 1993

INVENTOR(S) : Vince et al.

It is certified that error appears in the above-identified patent and that said Letters Patent is hereby corrected as shown below:

Column 11, line 26, change "cyclopenten-1-yl ]-6-purine-6-one" to -- cyclopenten-1-yl]-6H-purine-6-one --

Column 11, line 36, change "penten-1ols", --penten-1-ols--.

Column 11, line 64, change "cis-4-(Triphenylmethoxy)methyl[-2-cyclopenten-1-ol" to --cis-4-[(Triphenylmethoxy)methyl]-2-cyclopenten-1-ol--.

Column 11, line 65, change "1-(nButylcarbonate) (IVa)" to --1-(n-Butylcarbonate) (IVa)--.

Column 12, line 20, change "cyclopentenl-yl]-9H" to --cyclopenten-1-yl]-9H--.

Column 12, line 28, change "y)methyl" to --y)-methyl--.

Column 12, line 35, change "-9-[4 (hydroxyme-" to ---9-[4-(hydroxyme---.

Column 12, line 66, change "4Acetate (X)" to --4-Acetate (X)--.

Column 13, line 24, change "-cvclopentene" to ---cyclopentene--.

Column 13, line 26, change "tris(dibenzylideneacetone)dipal-" to -- tris(dibenzylideneacetone)-dipal---.

Column 13, line 28, change "[Pd2(DBA)" to --[Pd$_2$(DBA)--.

Column 13, line 68, change "[$\alpha$]D$_{20}$=" to --[$\alpha$]D$^{20}$=--.

Column 14, line 42, change "-9-4-(hydroxymethyl)" to ---9-[4-(hydroxymethyl)--.

UNITED STATES PATENT AND TRADEMARK OFFICE
CERTIFICATE OF CORRECTION

PATENT NO.    :    5,241,069
DATED         :    August 31, 1993
INVENTOR(S)   :    Vince et al.

It is certified that error appears in the above-identified patent and that said Letters Patent is hereby corrected as shown below:

Column 14, line 62, change "at -°C" to --at -20°C--.

Column 15, line 3, change "(IR-cis)-2-Amino-1.9" to --(IR-cis)-2-Amino-1,9--.

Column 15, line 4, change "-purin-6one" to ---purin-6-one--.

Column 15, line 5, change "1R-cisconfiguration)" to --1R-cis-configuration)--.

Column 16, line 4, change "1 1/2 Celite" to --1 1/2" Celite--.

Column 16, line 16, change "-purin-6one" to ---purin-6-one--.

Column 16, line 33, change "-cyclopenten-1-yl]-]-9H-" to --cyclopenten-1-yl]-9H---

Signed and Sealed this

Twenty-ninth Day of November, 1994

Attest:

BRUCE LEHMAN

*Attesting Officer*    Commissioner of Patents and Trademarks